United States Patent [19]

Yanagida et al.

[11] Patent Number: 5,798,109
[45] Date of Patent: Aug. 25, 1998

[54] EXTERNAL SKIN TREATMENT COMPOSITION

[75] Inventors: Takeshi Yanagida; Okihiko Sakamoto, both of Yokohama, Japan

[73] Assignee: Shiseido Company, Ltd., Tokyo, Japan

[21] Appl. No.: 699,854

[22] Filed: Aug. 20, 1996

Related U.S. Application Data

[63] Continuation of Ser. No. 416,472, Apr. 4, 1995, abandoned, which is a continuation of Ser. No. 204,285, filed as PCT/JP93/00970, Jul. 13, 1993, abandoned.

[30] Foreign Application Priority Data

Jul. 13, 1992 [JP] Japan .................... 4-227740
Jul. 13, 1992 [JP] Japan .................... 4-227741

[51] Int. Cl.$^6$ ................................ A61K 7/48
[52] U.S. Cl. ................ 424/401; 424/78; 424/70.11
[58] Field of Search ............... 424/401, 78, 70.11

[56] References Cited

U.S. PATENT DOCUMENTS

| | | | |
|---|---|---|---|
| 4,826,828 | 5/1989 | Wilmott et al. | 514/725 |
| 4,992,265 | 2/1991 | Davis et al. | 424/70 |
| 5,082,661 | 1/1992 | Melnik et al. | 424/401 |
| 5,089,269 | 2/1992 | Noda et al. | 424/456 |
| 5,122,418 | 6/1992 | Nakane et al. | 424/401 |
| 5,124,320 | 6/1992 | Ivy et al. | 514/159 |

FOREIGN PATENT DOCUMENTS

| | | |
|---|---|---|
| 0 255 364 | 2/1988 | European Pat. Off. . |
| 0 440 398 | 8/1991 | European Pat. Off. . |
| 54-26336 | 2/1979 | Japan . |
| 62-419 | 1/1987 | Japan . |
| 63-2926 | 1/1988 | Japan . |
| 63-135309 | 6/1988 | Japan . |
| A-63-258807 | 10/1988 | Japan . |
| A-64-40412 | 2/1989 | Japan . |
| 1-186811 | 7/1989 | Japan . |
| 1-246208 | 10/1989 | Japan . |
| 2-142713 | 5/1990 | Japan . |
| A-2-502546 | 8/1990 | Japan . |
| 86/06275 | 11/1986 | WIPO . |
| PCT/US88/04539 | 12/1988 | WIPO . |

*Primary Examiner*—Thurman K. Page
*Assistant Examiner*—D. Faulkner
*Attorney, Agent, or Firm*—Foley & Lardner

[57] ABSTRACT

An external skin treatment composition comprising (a) vitamin A and (b) (i) at least one kind of powder or (ii) at least one silicone oil selected from the group consisting of dimethyl polysiloxane and methylphenyl polysiloxane having a viscosity of 2–20 cs at 25° C.

8 Claims, No Drawings

EXTERNAL SKIN TREATMENT COMPOSITION

This application is a continuation of application Ser. No. 08/416,472, filed Apr. 4, 1995, which is a continuation of 08/204,285, filed on Mar. 10, 1994, which is the National Phase of PCT/JP93/00970, filed Jul. 13, 1993.

TECHNICAL FIELD

The present invention relates to an external skin treatment composition and, more specifically, it relates to an external skin treatment composition having a suppressed stickiness caused by vitamin A and having remarkably improved effects.

BACKGROUND ART

It is known in the art that vitamin A is an effective component capable of preventing and treating skin hyperkeratosis and of preventing and recovering skin aging. However, vitamin A has a strong sticky feeling when applied, in addition to the above-mentioned effects, and therefore, this is a weakness of vitamin A when formulated into an external skin treatment composition.

DISCLOSURE OF THE INVENTION

Accordingly, the object of the present invention is to provide an external skin treatment composition capable of preventing stickiness caused by vitamin A, when formulated into an external skin treatment composition, and capable of remarkably improving the usability of vitamin A.

In accordance with the present invention, there is provided an external skin treatment composition comprising (a) vitamin A and (b) (i) at least one kind of powder or (ii) at least one silicone oil selected from the group consisting of dimethyl polysiloxane and methylphenyl polysiloxane having a viscosity of 2-20 cs at 25° C.

BEST MODE FOR CARRYING OUT THE INVENTION

Vitamin A used in the present invention is also called retinol and all-trans products or 13-cis products can be preferably used, but the mixture thereof can also be used.

There are no limitations to the amounts of vitamin A formulated into the external skin treatment composition according to the present invention, but the preferable amount is 0.0001 to 5% by weight, more preferably 0.001 to 0.5% by weight, in view of the effect of vitamin A to the skin.

The powders used in the present invention include, for example, organic polymer powders such as nylon powder, polyethylene powder, cellulose powder, acrylic resin, etc., inorganic pigments, sintered pigments, organic pigments, such as mica, sericite, talc, kaolin, calcium carbonate, magnesium carbonate, zinc white, titanium dioxide, red iron oxide, yellow iron oxide, black iron oxide, ultramarine, titanium coated mica, bismuth oxychloride, blood red, caking pigment, ultramarine pink, chromium hydroxide, titanated mica, yellow iron oxide, chromium oxide, aluminum chromium oxide, Prussian blue, black iron oxide, carbon black, magnesium silicate, mica, zirconium oxide, magnesium oxide, zinc oxide, titanium oxide, light calcium carbonate, heavy calcium carbonate, light magnesium carbonate, heavy magnesium carbonate, calamine, etc. and those obtained by appropriately surface treating of these powders. There are no specific limitation to the particle size of these powders, but preferably, the average particle size is 0.01 to 20 µm.

The amount of the powder formulated according to the present invention is preferably 0.01% by weight or more and more preferably 0.1 to 80% by weight, in the total amount of the external skin treatment composition.

The silicon oil (i.e., dimethyl polysiloxane or methylphenyl siloxane) used in the present invention has a viscosity of 2–20 cs (25° C.), preferably 5–20 cs (25° C.). The silicone oils having a purity conventionally used for an external skin treatment composition can be used in the present invention. Those having a viscosity of less than 2 cs are not preferable from a viewpoint of safety to the skin. On the other hand, when the viscosity is more than 20 cs, there are no problems from the safety standpoints, but the intended effects of suppressing the stickiness according to the present invention are not sufficient. Furthermore, there are no limitations for the methylphenyl polysiloxane if they are usable for external skin treatment agent.

There are no specific limitations to the amount of the silicone oil formulated according to the present invention, but the amount is preferably 0.001–80.0% by weight, more preferably 1–80% by weight, based upon the total weight of the external skin treatment composition, in view of suppressing the stickiness of vitamin A.

The external skin treatment composition according to the present invention can be in any form of bases, for example, in the form of a solution type, a solubilized type, an emulsified type, powder dispersion type, water-oil two layer type, water-oil-powder three layer type, etc. The applications thereof are also widely spread in, for example, basic cosmetics such as cosmetic lotions, emulsions, creams, packs, etc., make-up cosmetics such as lipsticks, foundations, mascaras, eyeshadows, eyeliners, cosmetic bases, eyebrow pencils, calamine lotions, etc., hair cosmetics such as shampoos, rinses, hair tonics, etc., and other cosmetics, and quasi-drugs. Among these, when used in cosmetic lotions, emulsions, creams, the present invention can prove its true effects. This is because the stickiness due to humectants is generally especially felt in the case of cosmetic lotions and the stickiness due to the oily components in the bases is further felt in the case of emulsions and creams, etc.

In addition to the above-mentioned essential components, the external skin treatment composition according to the present invention may optionally contain various components conventionally formulated into cosmetics, quasi-drugs such as humectants, surfactants, preservatives, water, alcohols, thickeners, the other oil components, powders, drugs, chelating agents, perfumes (or flavours), colorants, UV absorbers, etc.

INDUSTRIAL APPLICABILITY

The external skin treatment composition according to the present invention is effective as an external skin treatment agent having no stickiness due to vitamin A, and good or excellent stability and safety, in spite of the fact that the external skin treatment composition is excellent, due to the formulation of vitamin A, in the prevention and treatment of skin hyperkeratosis and the prevention and recovery of skin aging.

EXAMPLES

The present invention will now be further illustrated by no means limited to, the following Examples, in which the amounts formulated are "% by weight".

Example 1-1: Cosmetic oil

| | % |
|---|---|
| Olive oil | 50.0 |
| Isopropyl myristate | 20.0 |
| Squalane | 20.0 |
| Vitamin A | 5.0 |
| Powder (talc) | 5.0 |

Comparative Example 1-1

The cosmetic oil of Comparative Example 1-1 was obtained in the same manner as in Example 1-1 except that the powder was removed.

The useability (i.e., stickiness) of Example 1-1 and Comparative Example 1-1 was evaluated by the judgement of a panel composed of 10 women's beauty specialists, who actually use The Samples.

(Evaluation standard)

A: No stickiness

B: Slight stickiness, but practically acceptable

C: Sticky

D: Remarkable stickiness

The results are shown in Table 1-1.

TABLE 1-1

| | Evaluation of feeling upon use by cosmetic technical experts | | | | | | | | | Overall evaluation |
|---|---|---|---|---|---|---|---|---|---|---|
| Example 1-1 | A | A | A | A | A | B | A | A | A | A |
| Comparative Example 1-1 | C | D | D | B | C | B | C | D | D | C | C |

As is clear from the above results, the powder prevents stickiness of vitamin A.

Example 1-2: Foundation

| | % |
|---|---|
| (Oil phase) | |
| Stearyl alcohol | 3.0 |
| Stearic acid | 2.0 |
| Squalane | 5.0 |
| POE(25) Cetyl ether | 1.0 |
| Glyceryl monostearate | 1.0 |
| Ethyl paraben | 0.2 |
| Vitamin A | 0.5 |
| (Powder phase) | |
| Titanium dioxide | 3.0 |
| Talc | 3.0 |
| Kaolin | 1.4 |
| Iron oxide | 2.6 |
| (Aqueous phase) | |
| Propylene glycol | 3.0 |
| Triethanolamine | 1.0 |
| Purified water | Balance |

(Preparation method)

The oil phase was heated under stirring, followed by dispersing the powder phase therein. The resultant dispersion was added to the aqueous phase similarly heated under stirring, to form the emulsion. The emulsion thus obtained was cooled under stirring to form the foundation.

Example 1-3: Compact foundation

| | % |
|---|---|
| Methylphenylpolysiloxane (degree of polymerization 250) | 15.0 |
| Liquid paraffin | 3.0 |
| Isopropyl myristate | 2.0 |
| Stearic acid | 1.0 |
| Ethyl paraben | 0.5 |
| Vitamin A | 1.0 |
| Powder preparation* | 77.5 |

*Powder preparation: powder comprising $TiO_2$ 7.0, talc 52.2, kaolin 15.0, and iron oxide 4.8 (all in wt %).

(Preparation method)

The compact foundation was obtained in a conventional manner.

Example 1-4: Foundation lotion

| | % |
|---|---|
| (Oil phase) | |
| Stearic acid | 2.0 |
| Cetanol | 0.3 |
| Liquid paraffin | 5.0 |
| Butyl paraben | 0.05 |
| POE(10) oleate | 1.0 |
| Sorbitan trioleate | 1.0 |
| Vitamin A | 10.0 |
| (Powder phase) | |
| Powder preparation* | 10.5 |
| (Aqueous phase) | |
| Ethanol | 5.0 |
| Propylene glycol | 5.0 |
| Triethanolamine | 1.0 |
| Carboxymethyl cellulose | 0.3 |
| Hibitane-gluconate Digluconate | 0.05 |
| Purified water | Balance |

*Powder preparation: Powder comprising $TiO_2$ 6.0, talc 6.2, kaolin 3.0, and red iron oxide 1.5 (all in wt %).

(Preparation method)

According to Example 1-2

Example 1-5: Oily foundation

| | % |
|---|---|
| Vitamin A | 0.1 |
| Powder preparation* | 43.0 |
| Microcrystalline wax | 10.0 |
| Sorbitan sesquioleate | 1.0 |
| Propyl paraben | 0.5 |
| Liquid paraffin | Balance |

*Powder preparation: Powder comprising $TiO_2$ 15.0, kaolin 25.0 and iron oxides 2.0 (all in wt %).

(Preparation method)

The components other than the powder preparation and vitamin A were dissolved by heating and stirring, followed by adding the powder preparation and vitamin A. The mixture was uniformly mixed, while the overall temperature was maintained. The mixture was filled in an inner dish, followed by cooling to obtain the oily foundation.

Example 1-6: Eyeshadow

|  | % |
| --- | --- |
| Powder preparation* | 92.1 |
| Beeswax | 2.0 |
| Hexadecyl palmitate | 5.0 |
| Glyceryl monostearate | 0.5 |
| Vitamin A | 0.2 |
| Perfume | 0.3 |

*Powder preparation: Powder comprising TiO$_2$ 5.0, kaolin 45.5, red iron oxide 6.0, and iron oxide (all in wt %).

(Preparation method)
According to Example 1-2

Example 1-7: Calamin lotion

|  | % |
| --- | --- |
| Zinc | 1.3 |
| Serisite | 3.0 |
| Iron oxide | 0.05 |
| Glycerol | 2.0 |
| Camphor | 0.2 |
| Phenol | 10.0 |
| POE(60) hydrogenated castor oil | 0.6 |
| Vitamin A | 0.001 |
| Purified water | Balance |

(Preparation method)

The calamin lotion was obtained by sufficiently mixing all the components under stirring.

Example 1-8: Base cream

|  | % |
| --- | --- |
| Propylene glycol | 5.0 |
| Potassium hydroxide | 0.2 |
| Glycerol | 3.0 |
| Talc | 1.0 |
| Kaolin | 2.0 |
| Iron oxide | 0.1 |
| Liquid paraffin | 10.0 |
| Vaseline | 5.0 |
| Stearic acid | 2.0 |
| Cetyl alcohol | 2.0 |
| Lanolin | 2.0 |
| Stearic monoglyceride | 2.0 |
| Ethyl paraben | 0.3 |
| Perfume | 0.2 |
| Isopropyl myristate | 0.5 |
| Vitamin A | 1.0 |
| Purified water | Balance |

(Preparation method)

The base cream was obtained according to a conventional manner.

Example 1-9: Night cream

|  | % |
| --- | --- |
| Liquid paraffin | 18.0 |
| Vaseline | 7.0 |
| Isopropyl myristate | 5.0 |
| Polyethylene powder | 4.0 |
| Butyl paraben | 0.2 |
| Vitamin A | 0.1 |
| Diglycerine monooleate | 2.0 |
| Diglycerine triisostearate | 2.0 |
| Glycerol | 7.0 |
| Cellulose powder | 3.0 |
| Yellow iron oxide | 0.05 |
| Purified water | Balance |

(Preparation method)

The night cream was obtained according to a conventional manner.

The products of Examples 1-2 to 1-9 were external skin treatment agents, which were excellent in the prevention and treatment of skin hyperkeratosis and the prevention and recovery of skin aging and also which did not exhibit roughening.

Example 2-1: Cosmetic lotion

|  | % |
| --- | --- |
| Ethanol | 20.0 |
| 1,3-Butylene glycol | 5.0 |
| Vitamin A | 0.0001 |
| Polyoxyethylene (50 mol) oleyl ether | 0.8 |
| Ethyl paraben | 0.1 |
| Dimethyl polysiloxane (10 cs) | 0.001 |
| Purified water | Balance |

(Preparation method)

In ethanol, vitamin A, dimethyl polysiloxane, POE oleyl ether and ethyl paraben were dissolved. Separately, the purified water and 1,3-butylene glycol were dissolved. The ethanol phase was added to the aqueous phase, followed by solubilizing to obtain the cosmetic lotion.

Comparative Example 2-1

The cosmetic oil of Comparative Example 2-1 was obtained in the same manner as in Example 2-1 except that the powder was removed.

The useability (i.e., stickiness) of Example 2-1 and Comparative Example 2-1 was evaluated by the judgement of a panel composed of 10 women's beauty specialists, who actually use The Samples. The results are shown in Table 2-1.

TABLE 2-1

|  | Evaluation of feeling upon use by cosmetic technical experts | | | | | | | | | | Overall evaluation |
| --- | --- | --- | --- | --- | --- | --- | --- | --- | --- | --- | --- |
| Example 2-1 | A | A | A | A | A | B | A | A | A | | A |
| Comparative Example 2-1 | C | D | D | B | C | B | C | D | D | C | C |

As is clear from the above results, the silicone oil prevents the stickiness of vitamin A.

Example 2-2: Cleansing cream

| | | % |
|---|---|---|
| (A) | Cetanol | 3.0 |
| | Beeswax | 1.0 |
| | Solid paraffin | 1.0 |
| | Stearic acid | 2.0 |
| | Vaseline | 10.0 |
| | Liquid paraffin | 15.0 |
| | POE(20) Sorbitan stearate | 2.4 |
| | Diglycerine distearate | 2.6 |
| | Vitamin A | 0.5 |
| | Nylon powder (Ave. particle size 1 μ) | 3.0 |
| | Methylphenyl polysiloxane (degree of polymerization 250) | 20.0 |
| | Propyl paraben | 0.3 |
| | Perfume | 0.3 |
| (B) | Dipropylene glycol | 5.0 |
| | Potassium hydroxide | 0.08 |
| | Purified water | Balance |

(Preparation method)

The oil phase (A) and the aqueous phase (B) were separately dissolved by heating and stirring. The oil phase was added to the aqueous phase, followed by emulsifying and cooling, to obtain the cream.

Example 2-3: Nutritious emulsion

| | | % |
|---|---|---|
| (A) | Beeswax | 1.0 |
| | Vaseline | 2.0 |
| | Deodored lanolin | 1.5 |
| | Jojoba oil | 6.0 |
| | Cetyl isooctanoate | 4.0 |
| | Glyceryl monostearate | 2.0 |
| | POE-20-octyl dodecanol | 2.0 |
| | Ethyl paraben | 0.2 |
| | Butyl paraben | 0.1 |
| | Vitamin A | 0.3 |
| | Dimethyl polysiloxane (20 cs) | 1.0 |
| | Perfume | 0.3 |
| (B) | Dipropylene glycol | 2.0 |
| | Carboxyvinyl polymer | 0.2 |
| | L-alginine | 0.2 |
| | Purified water | Balance |

(Preparation method)

According to Example 2-2

Example 2-4: Foundation

| | | % |
|---|---|---|
| (A) | Cetanol | 3.5 |
| | Stearic acid | 2.0 |
| | Deodored lanolin | 5.0 |
| | Vaseline | 2.0 |
| | Squalane | 8.0 |
| | Glyderyl monooleate | 2.5 |
| | POE(10) behenyl alcohol | 0.5 |
| | Ethyl paraben | 0.2 |
| | Butyl paraben | 0.2 |
| | Vitamin A | 5.0 |
| | Dimethyl polysiloxane (2 cs) | 0.5 |
| | 1,3-Butylene glycol | 2.0 |
| | Powder preparation* | 15.0 |

-continued

| | % |
|---|---|
| Triethanolamine | 0.25 |
| Purified water | Balance |

*Powder preparation: Powder comprising titanium dioxide 5.0, kaolin 3.0, talc 0.5, and iron oxide 2.0 (all in wt %).

(Preparation method)

According to Example 2-4

Example 2-5: Cosmetic lotion

| | | % |
|---|---|---|
| (A) | Purified water | Total amount to 100 |
| | Glycerol | 2.0 |
| | 1,3-Butylene glycol | 2.0 |
| (B) | Ethanol | 15.0 |
| | Purified lecithin | 0.02 |
| | POE(60) hydrogenated castor oil | 1.0 |
| | Vitamin A | 0.00001 |
| | Dimethyl polysiloxane (6 cs) | 0.001 |
| | Perfume | 0.05 |
| | Methyl paraben | 0.1 |

(Preparation method)

The aqueous phase (A) and the alcoholic portion (B) were separately dissolved uniformly and the alcoholic portion was added to the aqueous phase, followed by solubilizing to obtain the cosmetic lotion.

Example 2-6: Aqueous essence

| | | % |
|---|---|---|
| (A) | Purified water | Total amount to 100 |
| | Glycerol | 2.0 |
| | 1,3-Butylene glycol | 10.0 |
| | Maltitol | 2.0 |
| | Sodium hyaluronate | 0.2 |
| | Dipropylene glycol | 5.0 |
| | Carboxyvinyl polymer | 0.5 |
| (B) | Ethanol | 5.0 |
| | POE(60) hydrogenated castor oil | 1.0 |
| | Vitamin A | 0.1 |
| | Methylphenyl polysiloxane | 3.0 |
| | Perfume | 0.05 |
| | Methyl paraben | 0.2 |
| (C) | Potassium hydroxide | 0.1 |

(Preparation method)

The aqueous phase (A) and the alcoholic portion (B) were separately dissolved uniformly and the alcoholic portion was added to the aqueous phase, followed by solubilizing, and the potassium hydroxide (C) was added thereto, to obtain the cosmetic lotion.

Example 2-7: Cosmetic oil

| | % |
|---|---|
| Dimethyl polysiloxane (6 cs) | 40.0 |
| Methylphenyl polysiloxane | 40.0 |
| Isopropyl myristate | 15.0 |

|  | % |
| --- | --- |
| Vitamin A | 5.0 |
| Perfume | q.s. |

(Preparation method)

The cosmetic oil was obtained in a conventional manner.

Example 2-8: Night cream

|  | % |
| --- | --- |
| Squalane | 10.0 |
| Isopropyl myristate | 5.0 |
| Methylphenyl polysiloxane | 5.0 |
| Dimethyl polysiloxane (5 cs) | 7.0 |
| Vaseline | 4.0 |
| Diglycerine diisostearate | 3.0 |
| Glyceryl monooleate | 1.0 |
| Butyl paraben | 0.1 |
| Vitamin A | 0.3 |
| Glycerol | 20.0 |
| Dipropylene glycol | 3.0 |
| Magnesium sulfate | 0.3 |
| Purified water | Balance |

(Preparation method)

The night cream was obtained in accordance with a conventional manner.

The external skin treatment agents of Examples 2-2 to 2-8 were excellent in the prevention and treatment of skin hyperkeratosis and the prevention and recovery of skin aging and also were not sticky.

We claim:

1. A method for preventing stickiness caused by vitamin A, said method comprising:

adding to and mixing with an external skin treatment composition comprising vitamin A, a component which includes (i) at least one powder or (ii) at least one silicone oil selected from the group consisting of dimethyl polysiloxane and methylphenyl polysiloxane having a viscosity of 2–20 cs at 25° C., to form a formulated composition; and continuing adding and mixing said component with said external skin treatment composition, until a desired reduction of stickiness is achieved.

2. A method for preventing stickiness caused by vitamin A and a method for treating skin comprising:

adding to and mixing with an external skin treatment composition comprising vitamin A, a component which includes (i) at least one powder or (ii) at least one silicone oil selected from the group consisting of dimethyl polysiloxane and methylphenyl polysiloxane having a viscosity of 2–20 cs at 25° C., to form a formulated composition; and continuing adding and mixing said component with said external skin treatment composition, until a desired reduction of stickiness is achieved, and adding the formulated composition to the skin of a user.

3. A method for preventing stickiness caused by vitamin A and a method for treating skin comprising:

adding to and mixing with an external skin treatment composition comprising vitamin A, a component which includes (i) at least one powder or (ii) at least one silicone oil selected from the group consisting of dimethyl polysiloxane and methylphenyl polysiloxane having a viscosity of 2–20 cs at 25° C., to form a formulated composition; and continuing adding and mixing said component with said external skin treatment composition, until a desired reduction of stickiness is achieved, and adding the formulated composition to the skin of a user, wherein the formulated composition is in a form selected from the group consisting of a cosmetic lotion, an emulsion or a cream.

4. A method as claimed in claim 1, wherein the amount of vitamin A formulated in the composition is 0.0001 to 5.0% by weight, based upon the total amount of the composition.

5. A method as claimed in claim 1, wherein the component is at least one powder selected from the group consisting of polymer powders, inorganic powders, sintered pigments, and organic pigments.

6. A method as claimed in claim 1, wherein the amount of the at least one powder formulated into the composition is 0.01 to 80% by weight, based upon the total weight of the external skin treatment composition.

7. A method as claimed in claim 1, wherein the component is the at least one silicone oil.

8. A method as claimed in claim 1, wherein the amount of the at least one silicone oil formulated into the composition is 0.001 to 80% by weight, based upon the total weight of the external skin treatment composition.

* * * * *